(12) United States Patent
Sergere

(10) Patent No.: US 8,304,002 B2
(45) Date of Patent: Nov. 6, 2012

(54) FENUGREEK EXTRACT FOR TREATING HUMAN AND ANIMAL DISEASES INVOLVING FLAGELLATE PARASITES

(75) Inventor: Jean Christophe Sergere, Etroussat (FR)

(73) Assignee: Setubio S.A.S. (FR)

( * ) Notice: Subject to any disclaimer, the term of this patent is extended or adjusted under 35 U.S.C. 154(b) by 96 days.

(21) Appl. No.: 12/945,050

(22) Filed: Nov. 12, 2010

(65) Prior Publication Data

US 2011/0123656 A1     May 26, 2011

Related U.S. Application Data

(63) Continuation of application No. PCT/FR2009/050780, filed on Apr. 28, 2009.

(30) Foreign Application Priority Data

May 13, 2008  (FR) ...................... 08 53068

(51) Int. Cl.
*A61K 36/00* (2006.01)
*A61P 33/02* (2006.01)

(52) U.S. Cl. ...................... 424/757; 424/725; 424/269.1

(58) Field of Classification Search .......................... None
See application file for complete search history.

(56) References Cited

U.S. PATENT DOCUMENTS

2008/0183277 A1* 7/2008 Atanasoska et al. ......... 623/1.15

FOREIGN PATENT DOCUMENTS

| FR | 2833813 A1 | 6/2003 |
|---|---|---|
| JP | 2008011731 A | 1/2008 |
| WO | 2008003007 A2 | 1/2008 |

OTHER PUBLICATIONS

Viollon, Antagonist activities, in vitro, of certain essential oils and natural volatile compounds with regard to the increase in *Trichomonas vaginalis*, Fitoterapia, vol. LXVII No. 3, 1996.*
Blank et al, The principal flavor components of fenugreek (*Trigonella foenum-graecum* L.), ACS symposium series (1997), 660 (Spices), 12-28.*
Almeida et al, antigiardial activity of *Ocinum basilicum* essential, Parasitol Res (2007), 101: 443-452.*
McDougald, Blackhead disease (histomoniasis) in poultry, a critical review, Avian diseases (2005), vol. 49, No. 4: 462-76.*
El-Malky et al, Effect of green leaves and germination and boiling treatments of fenugreek and lupin seeds on chemical composition, serum glucose, lipid profile and hepatic enzymes of rats, Egyptian Journal of Biomedical Sciences (2007), 23, 39-59.*
International Search Report; PCT/FR2009/050780; Mar. 3, 2010; 3 pages.
Inayama, et al.; "Mixed Feed manufacture for Reducing Incidence Rate of Diarrhea in Young age Piglets, Comprises Lactose, Crude Protein, Anise and *Trigonella Foenum-Graecum*"; Thomason Scientific, London GB; 2008; 3 pages.
Francis, et al.; "The Biological Action of Saponins in Animal Systems: A Review"; British Journal of Nutrition; Cambridge University Press; vol. 88 No. 6; 2002; 19 pages.

* cited by examiner

*Primary Examiner* — Qiuwen Mi

(74) *Attorney, Agent, or Firm* — St. Onge Steward Johnston & Reens LLC

(57) ABSTRACT

Use of an extract of fenugreek to obtain a formulation for the preventive or curative treatment of human or animal diseases involving flagellated protozoa belonging to the Metamonada phylum.

9 Claims, 7 Drawing Sheets

FENUGREEK EXTRACT FOR TREATING HUMAN AND ANIMAL DISEASES INVOLVING FLAGELLATE PARASITES

CROSS-REFERENCE TO RELATED APPLICATIONS

The present application is a continuation of pending International patent application PCT/FR2009/050780 filed on Apr. 28, 2009, which designates the United States and claims priority from French patent application 0853068 filed on May 13, 2008, the content of which is incorporated herein by reference.

FIELD OF THE INVENTION

The invention concerns an extract of fenugreek used alone or incorporated into a dietary supplement or a pharmaceutical formulation for treating human or animal diseases in which flagellate parasites are implicated.

BACKGROUND OF THE INVENTION

The invention is particularly illustrated in relation to flagellate parasites, such as *Histomonas meleagridis* and *Trichomonas vaginalis* although it can apply to any flagellate parasite the structure and physiology of which is similar to that of the above-mentioned parasites belonging to the phylum Metamonada.

The parasite *Histomonas meleagridis* is responsible for an infectious parasitic disease of galliform birds called histomoniasis. This disease is a typhlohepatitis particularly infecting turkeys. It appears as a sulphur-yellow diarrhea often leading to high mortality. Cyanosis observed in the fleshy appendages of the head has given this disease the name of blackhead disease. Other clinical symptoms are feathers spotted with droppings, anorexia, drowsiness, abnormal gait, the head held low or hidden under a wing. Considerable mortality is seen from the 14$^{th}$ day. Without treatment, more than 90% of the animals may die. Surviving galliform bird, in particular turkeys, show delayed growth relative to clinically unaffected birds.

Many different treatments have already been suggested to counter histomoniasis: the nitroimidazoles in particular, especially dimetridazole (DMZ), are very active against *Histomonas meleagridis*. However, because of their toxicity for consumers, this family of molecules has been withdrawn from the market. Albendazole and the other benzimidazoles proved to be ineffective in treating histomoniasis. The same applies to the other antibiotics currently authorised for sale, as well as to anticoccidial drugs such as roxarsone. Moreover, immunisation trials with attenuated strains have never worked.

Given this situation, the only conceivable prophylaxis consists of either separating the species or administering an effective anthelminthic against the protozoa.

In other words, the invention proposes to solve the problem of producing an effective formulation for prophylactic and curative treatment, particularly in galliform birds, of the protozoan *Histomonas meleagridis*.

The invention is also more particularly illustrated in relation to a flagellated protozoan *Trichomonas vaginalis* with physiology and structure similar to that of *Histomonas meleagridis*. *Trichomonas vaginalis* is a flagellated protozoan which develops in humans essentially localised in the urogenital region. It leads to an ubiquitous sexually transmitted disease known as trichommoniasis.

In women, clinical symptoms present as acute vulvo-vaginitis with a continuous frothy foul-smelling greenish yellow leucorrhoea, or valvular pruritus with a burning sensation. Complications are cervical neoplasia and premature delivery.

In men, trichommoniasis is asymptomatic and this contributes to the spread of the disease. Urethritis, epididymitis, prostatitis and even sterility can occur.

The products currently prescribed belong to the imidazole family, particularly metronidazole, ornidazole, secnidazole, tenonitrozole, and tinidazole. While effective, these products must be used with some care, in particular in pregnant or breast-feeding women.

In general terms, the problem to be solved is thus to produce a formulation which is effective for the prophylaxis and treatment of human or animal diseases involving flagellated protozoa, in particular *Histomonas meleagridis* and *Trichomonas vaginalis*, which, in addition, is neither cytotoxic nor mutagenic.

Surprisingly, the applicant has found and demonstrated that fenugreek has parasiticidal or parasitostatic properties as far as the previously mentioned protozoa are concerned and more generally concerning all flagellated protozoa belonging to the Metamonada phylum which have a similar structure and physiology to that of *Histomonas meleagridis* and *Trichomonas vaginalis*.

The document JP 2008011731 describes a formulation containing a fenugreek extract intended to treat diarrhea in piglets. The document FR-A-2 833 813 describes a formulation containing a fenugreek extract intended to treat coccidiosis.

SUMMARY OF THE INVENTION

The objective of the invention is first of all the use of an extract of fenugreek to obtain a formulation for the preventive or curative treatment of human or animal diseases involving flagellated protozoa belonging to the Metamonada phylum, in particular *Histomonas meleagridis* and *Trichomonas vaginalis*.

In an advantageous embodiment, the flagellated protozoa concerned by the invention belong to the Metamonada phylum, including the Parabasalia and Eopharyngia classes.

In particular, the extract is used for the treatment of histomoniasis in galliform birds, in particular poultry and more particularly turkeys, and for the treatment of trichommoniasis in men and/or women.

Fenugreek has the scientific name of *Trigonella foenumgraecum* and belongs to the Leguminosae family. Originally from North Africa and the Mediterranean basin, this annual plant has been grown for a long time in Asia, particularly in India and China. Fenugreek has many applications in humans or animals. Traditionally it can be used as a tonic to stimulate the appetite and improve digestion, as an orexigenic or to relieve irritation of the respiratory tract. More recently, research and clinical studies have shown that fenugreek can contribute to regulating blood glucose concentration in diabetes.

According to the invention, the whole plant or all the parts of the plant can be used.

In a first embodiment, the extract is obtained from the seeds. To advantage the seeds are dehusked and micronised (to a size in the order of 50 μm) or atomised (to a size of less than 50 μm).

In a second embodiment, the extract is obtained from the germ previously separated from the seeds after germination.

In practice, the dehusked seeds or the germs are macerated with stirring at ambient temperature and the solution is then centrifuged to recover just the supernatant.

It must be understood that fenugreek extract can be used as it is as or to greater advantage within a formulation, particularly a more complex pharmaceutical formulation in the presence of excipients. It can also be incorporated into a solid dietary supplement or a drink, particularly an aqueous drink.

The ingredients which could be used in the formulation, in particular in the form of a solid supplement, are, for example, wheat, maize, soya, soya oil, palm oil, or mineral salts, amino acids, vitamins and other sources of carbon, and more generally any compound which can be put into food.

When it is used in a formulation or dietary supplement or a drink, the extract will form between 0.1 and 5% by weight of the formulation, preferably between 0.5 and 5% by weight of the formulation.

When the extract is used in animals for the treatment of the flagellate parasites mentioned in this application and is in the form of a solid dietary supplement, it will be present at between 1 and 3 g/kg, to advantage 2 g/kg of the supplement.

When the extract is used in animals for the treatment of flagellate parasites mentioned in this application and is in the drinking water, it will be present at between 1 and 3 g/L, to advantage 2 g/L of the drink.

When the extract is used in humans for the treatment of flagellate parasites mentioned in this application and is in the form of a solid formulation, it will be present at between 1 and 3 g/kg, to advantage 2 g/kg of the formulation.

When the extract is used in humans for the treatment of flagellate parasites mentioned in this application and is in the form of a liquid formulation, it will be present at between 100 and 1000 µg/mL, to advantage 500 µg/mL of the formulation.

The formulation is generally administered orally. In this case, the preparation is generally administered as 0.5% of the formulation.

In the case of *Trichomonas vaginalis*, the extract is administered via the vaginal route.

As already stated, fenugreek extract can be used for the treatment of diseases which involve flagellated protozoa and, in addition to the previously mentioned protozoa, particularly the protozoa in the following list:

*Tetratrichomonas gallinarum*, *Trichomonas gallinae* which are intestinal parasites of galliform birds,
*Trichomonas foetus*, a parasite of the bovine genital tracts,
*Trichomonas equi*, an intestinal parasite of horses,
*Spironucleus vortens* a parasite of salmonidae fish,
*Hexamita meleagridis* a parasite in galliform birds,
*Giardia intestinalis* a parasite of humans.

BRIEF DESCRIPTION OF THE DRAWINGS

The invention and the advantages resulting from it are illustrated well by the following examples and the figures attached.

DETAILED DESCRIPTION OF THE INVENTION

Figure 1:
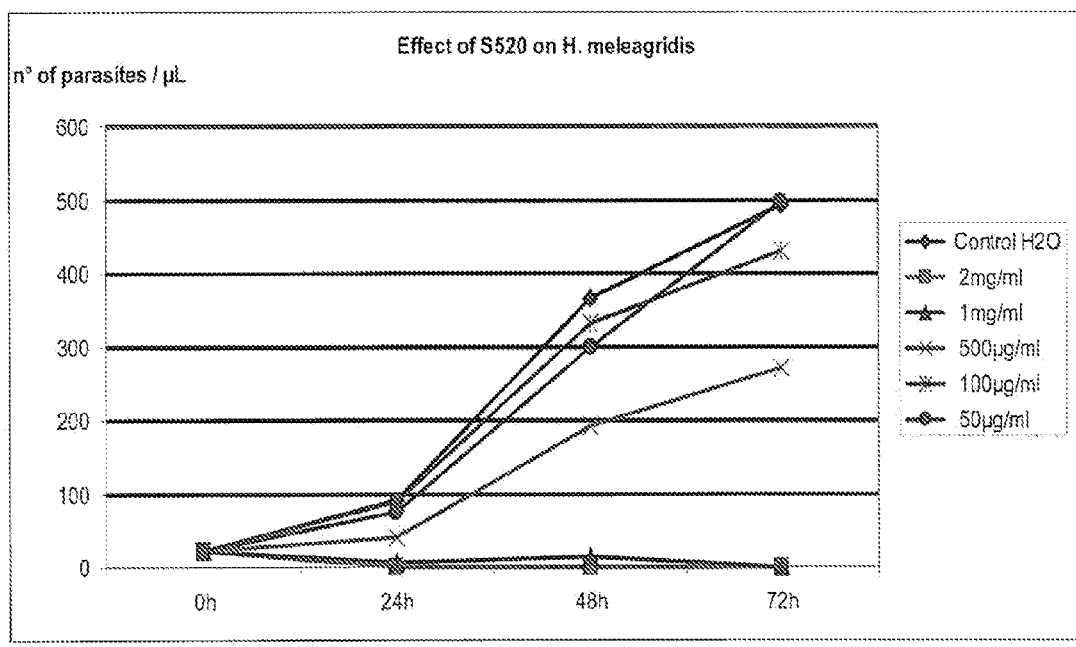
FIG. 1 is a graphical representation of the in vitro activity of the extract according to the invention on *H. meleagridis*.

Materials and Method
1.1. Preparation of the extract

Fenugreek extract is obtained by grinding the dehusked seeds, micronised to a particle size of 50 µm, and is then known as S520.

1 g of this powder is taken up into 5 mL of sterile water (concentration of 200 mg/mL).

The solution is stirred overnight at ambient temperature then centrifuged for 10 min at 16100 g at 4° C.

The supernatant is recovered and again centrifuged for 10 min at 16100 g at 4° C.

The supernatant is then stored in 1 mL aliquots at −80° C.

1.2. Culturing *Histomonas meleadridis*

The strain of *H. meleagridis* was isolated from the caeca of turkeys experimentally infested with eggs of the *H. gallinarum* worm. The parasites were cultured at 39° C. in sealed glass tubes containing 3 mL of supplemented M199 medium. They were transferred twice a week. To do this, 80 µL of preculture were added to 3 mL of fresh medium previously heated in a water bath to 39° C.

Supplemented M199 Medium:

| | |
|---|---|
| M199 | 42 mL |
| Horse serum | 5 mL |
| Rice starch solution | 4 mL | pH = 7.4

Rice Starch Solution: Carbon Source

| | |
|---|---|
| Rice starch | 0.6 g |
| NaCl | 0.325 g |
| NaHCO$_3$ | 0.05 g |
| CaCl$_2$ | 0.015 g |
| H•$_2$O qs 50 mL | |

1.3. Culture of the Bacterial Flora Associated with *H. meleaqridis*

An aliquot of *H. meleagridis* culture was taken.

Four serial dilutions ($10^{-4}$ to $10^{-7}$) were made in liquid tryptone soya medium. 20 µL of each dilution was spread onto tryptone soya agar medium. Incubation at 37° C. overnight.

1.4. Culture of *Trichomonas vaginalis*

The *T. vaginalis* strain was ATCC 30243 (reference strain).

The parasites were cultured in filtered Hollander medium at 35° C. They were transferred every 3 days. To do this, 80 µL of the culture were added to 3 mL of fresh medium previously heated in a water bath to 35° C.

Hollander Medium:

| | |
|---|---|
| Trypticase | 20.00 g |
| Yeast extract | 10.00 g |
| Maltose | 5.00 g |
| L-ascorbic acid | 1.00 g |
| KCl | 1.00 g |
| $KHCO_3$ | 1.00 g |
| $KH_2PO_4$ | 1.00 g |
| $K_2HPO_4$ | 1.00 g |
| $FeSO_4 \cdot 7H_2O$ | 0.18 g |
| $H_2O$ qs 1000 mL | | pH = 6.2

1.5. Parasite Counts

Counting was performed in a Malassez counting chamber after staining with 0.4% trypan blue.

The 100 fields of the chamber were counted.

1.6. Study of the Anti-*Histomonas* Activity

S520 was tested at different concentrations. A parasite count was performed three times after 72 h incubation. A negative control was included by replacing the extract with the solvent only (sterile water). To study the dose-dependent effect, each test was performed in triplicate, with different concentrations, counting the parasites at 24 h, 48 h and 72 h. A negative control was included by replacing the extract with the solvent only.

1.7. Study of the Anti-*Trichomonas* Activity

S520 was tested at 4 concentrations: 1 mg/mL, 500 µg/mL, 100 µg/mL and 50 µg/mL. The *T. vaginalis* cultures were counted after 24 h, 48 h and 72 h of incubation with the samples. The experiments were performed in triplicate.

1.8 Cytotoxicity Test 1.8.1 Culture of MRC5 Cells

The MRC5 cells (primary human foetal lung fibroblasts) were cultured in 25 or 75 cm² dishes in supplemented MEM (Minimum Essential Medium, *Life Technologies Gibco*), in a chamber at 37° C. and % $CO_2$.

500 mL of MEM was supplemented with foetal calf serum (10% final), glutamine 2 mM (5 mL), antibiotics (5 mL penicillin/streptomycin i.e. 0.1 mU/mL, 0.5 mL ampicillin i.e. 10 µg/ml, 0.25 mL gentamicin i.e. 25 µg/mL) and fungicides (5 mL fungizone i.e. 2.5 µg/mL).

When the cells reached confluence, they were trypsinised and transferred into 96-well plates at 1 to $2.10^5$ cells/well. They were then incubated at 37° C., 5% $CO_2$ for 24 h before starting the test.

The plates were duplicated for a protein assay after 24 and 48 h.

1.8.2. Protein Assay

This test consists of culturing the cells in the presence of extracts, then precipitating total proteins to determine their concentration.

The MRC5 cells were put into contact with 200 µL of supplemented MEM containing different concentrations of the extracts to be tested. Each extract was tested at 3 concentrations: 2 mg/mL, 1 mg/mL and 500 µg/mL. Each dilution was tested in triplicate to produce a mean.

Two controls were used:
  a negative control: cells in the supplemented MEM only
  a positive control: cells in the presence of a mixture of the supplemented MEM and 50% DMSO The plates were then incubated at 37° C., 5% $CO_2$ for 24 or 48 h. After 24 or 48 h, the medium containing the extracts was removed and replaced by fresh medium. The total proteins were precipitated by 50 µL of 50% trichloroacetic acid (TCA). After 2 hours of incubation at 4° C. the wells were washed with tap water. Once the plate had dried, 0.4% sulphorhodamine (SRB) was added to each well to stain the proteins. After 20 min incubation, the wells were rinsed with 1% acetic acid and the proteins solubilised in 10 mM tris-base buffer, pH 10.5. The contents of the wells were homogenised and the optical density read at 490 nm.

1.9 Reverse Mutation Test

The mutagenicity of the extracts was assessed using a kit marketed by a Canadian company (EBPI): Muta-Chromoplate™ Kit-S9. This chromotest kit is based on the most generally used and validated bacterial reverse mutation test, known as the Ames test. The test uses a mutant of *Salmonella typhimurium* with a mutation in the operon coding for histidine biosynthesis. When these bacteria are exposed to mutagenic agents, under certain conditions, reverse mutation appears and the initially histidine auxotrophic bacteria become prototrophic. Products are tested with or without activation by S9. This is a rat liver homogenate which mimics hepatic metabolism, and allows the product and its metabolites to be tested.

The day before the test, the bacterial lyophilisate was rehydrated with culture medium and then incubated at 37° C. for 16 to 18 h. The reaction medium and the S9 mixture were prepared according to the instructions provided in the kit. The reaction medium was added to all the tubes containing an extract to be tested. S9 was only added to tubes where the extract was tested with activation. 5 µL of *Salmonella typhimurium* (TA100) were added to each test tube with the exception of the sterility control. 200 µL of the mixture were transferred to each well of a 96-well plate: 1 plate for each control and 2 plates for each extract (one activated and one not activated). The plates were closed with the covers, put into sterile plastic bags to maintain the humidity and incubated for 5 days at 37° C.

Five controls were used:
  A sterility control (blank): reaction medium only
  A spontaneous reversion control without activation (Background 1): the bacteria and the reaction medium
  A spontaneous reversion control with activation (Background 2): the bacteria, the S9 mixture and the reaction medium
  A control with a mutagen without activation (Standard Mutagen 1): the bacteria, a mutagenic substance (sodium azide $NaN_3$) and the reaction medium
  A control with a mutagen with activation (Standard Mutagen 2): the bacteria, a mutagenic substance (2-amino-anthracene), the S9 mixture and the reaction medium 2/Results 2.1. Anti-Histomonas Activity of S520

As FIG. 1 shows, S520 is histomonicidal from 1 mg/mL and from 24 h. It slows proliferation of the parasite at 500 µg/mL (at 72 h: 51% inhibition). The effect is dose-dependent.

Figure 3:
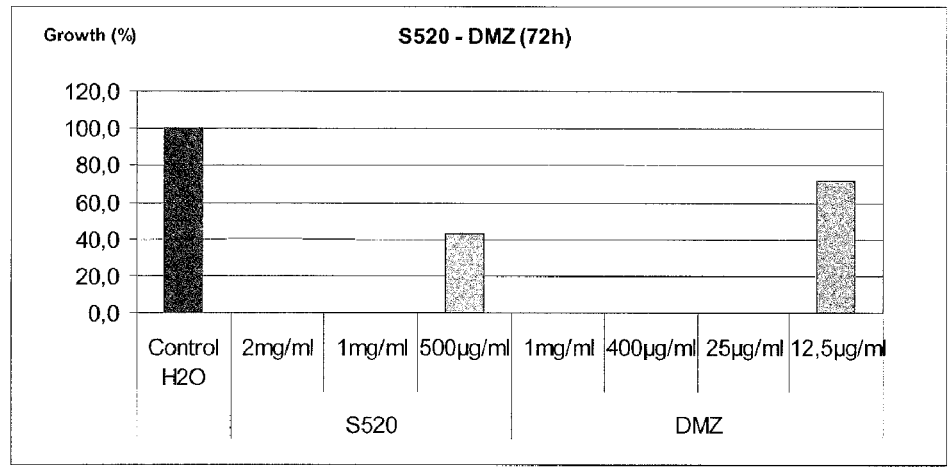
FIG. 3 is a graphical representation comparing the efficacy of the extract according to the invention with that of dimetridazole on the growth of *H. meleagridis*.

The efficacy was also compared with that of substances used against histomoniasis: PrismaFlag® (Santamix), Santagib® (Prisma) and Nifursol (FIG. 3). The results are expressed in percentage of growth relative to the control.

Figure 2:
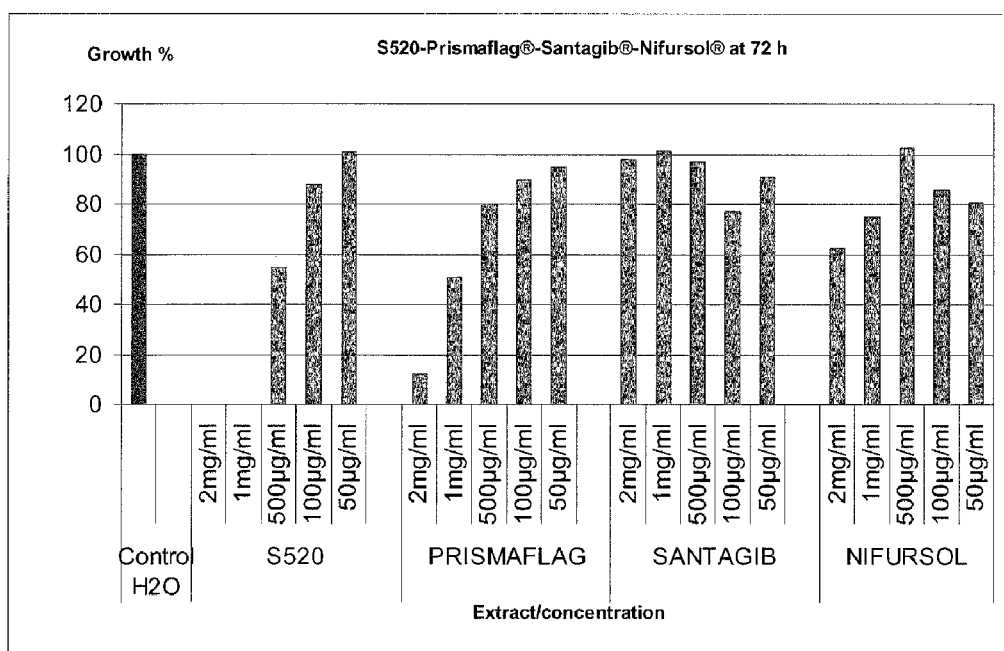
FIG. 2 is a graphical representation comparing the activity of the extract according to the invention on *H. meleagridis* compared with the reference product.

As FIG. 2 shows, PrismaFlag® is histomonostatic from 1 mg/mL (at 72 h: 88% inhibition at 2 mg/mL and 50% inhibition at 1 mg/mL). No significant effect of Santagib® was seen on the proliferation of *H. meleagridis*. Nifursol is slightly histomonostatic at 2 mg/mL (at 72 h: 38% inhibition).

At equal concentration, S520 is therefore the most effective extract for inhibiting the proliferation of *H. meleagridis*.

Finally S520 was tested in parallel with dimetridazole (DMZ). The results are shown in FIG. 3. As this figure shows, DMZ is a parasiticidal substance at 25 μg/mL, while DMZ is parasitostatic.

Figure 4:
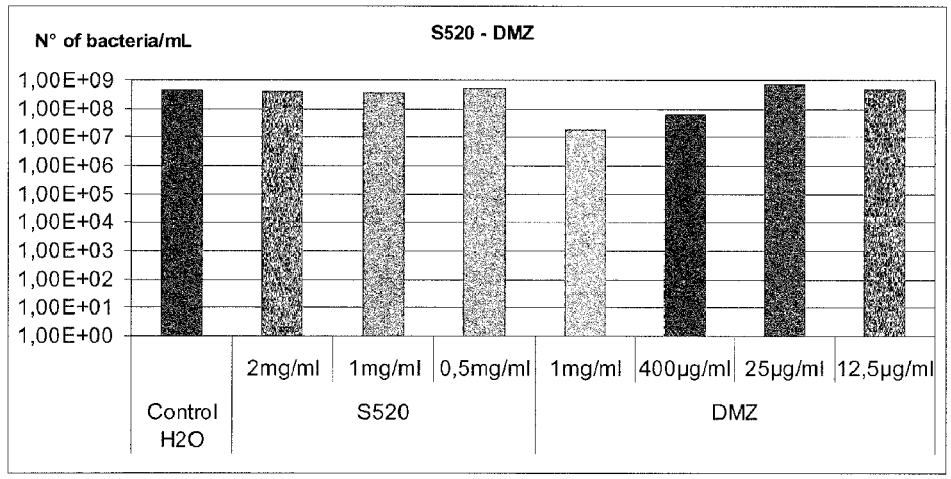
FIG. 4 is a graphical representation comparing the effects of the extract according to the invention with those of DMZ on the bacterial flora associated with *H. meleagridis*.

The effects of different concentrations of S520 and of DMZ on the associated bacterial flora after 48 h of culture were then compared. The results are expressed in number of bacteria per mL (FIG. 4). The extract S520 was histomonicidal from 1 mg/mL. It had no effect on the associated bacterial flora. Dimetridazole is histomonicidal from 25 μg/mL at 72 h. On the other hand it is bactericidal from 400 μg/mL.

Figure 5:
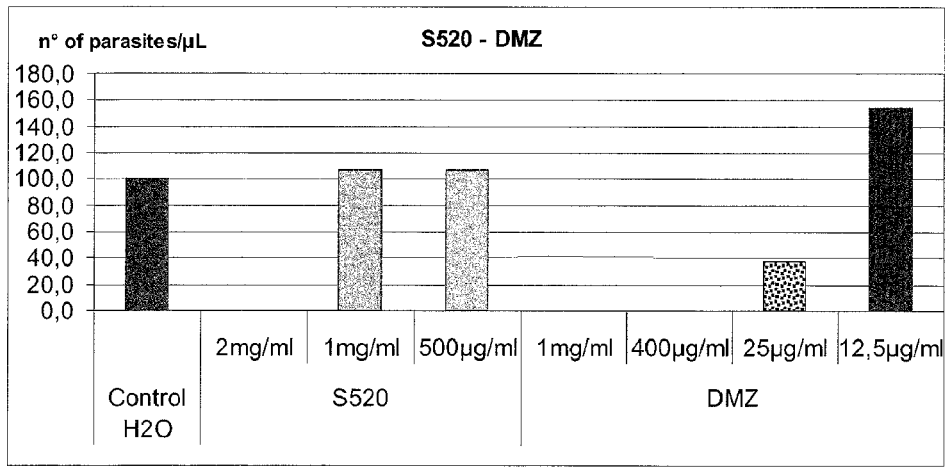
FIG. 5 is a graphical representation comparing the efficacy of the extract according to the invention with that of dimetridazole on the growth of *H. meleagridis* after transfer into a fresh medium.

After 72 h of treatment with S520 and DMZ, the parasites were put into fresh medium for 96 h to analyse the histomonicidal effect (FIG. 5).

S520: No regrowth of the culture at 2 mg/mL but regrowth at 1 mg/mL and 500 μg/mL.

This confirms that S520 at 2 mg/mL is histomonicidal. At 1 mg/mL a few parasites survived, it is therefore histomonostatic and not histomonicidal.

DMZ: No regrowth of the culture at 1 mg/mL and 400 μg/mL but regrowth at 25 μg/mL (but only about 30% of growth relative to the control) and at 12.5 μg/mL.

This confirms that DMZ is histomonicidal from 400 μg/mL. It seems to be histomonostatic only at 25 μg/mL as the regrowth of the culture indicates that some parasites survived the treatment. It should be noted that at a concentration of 400 μg/mL, DMZ acts on the associated flora (FIG. 4).

Figure 6:
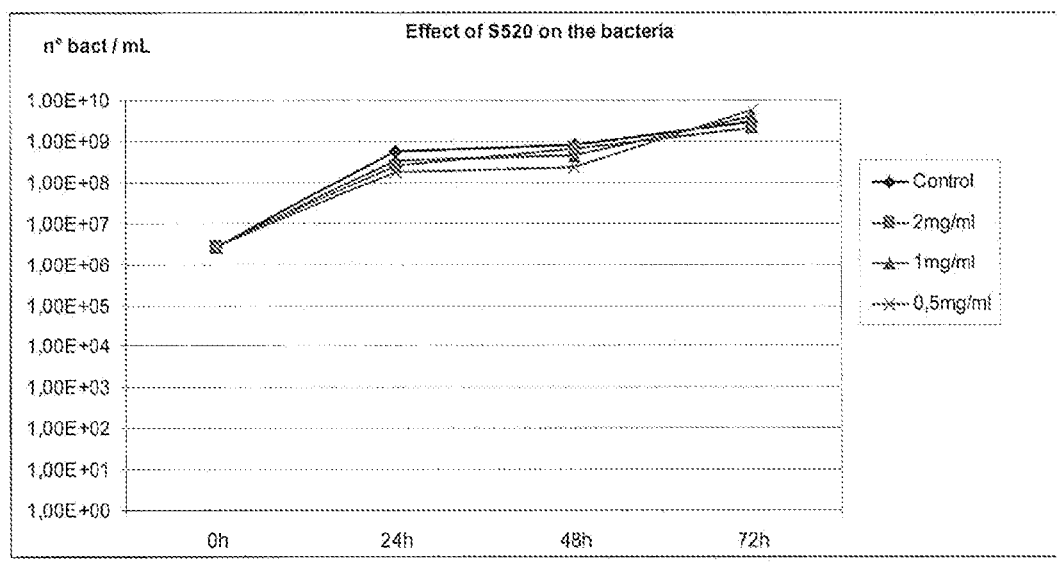
FIG. 6 is a graphical representation comparing the effects of the extract according to the invention with those of DMZ on the bacterial flora associated with *H. meleagridis* after 72 h.

The study performed over 72 h on the associated bacterial flora shows that the various concentrations of S520 have no effect on this flora (FIG. 6).

2.2. Cytotoxicity Test

Test performed on MRC5 cell cultures.

The extract was compared with three reference substances: PrismaFlag®, Santagib® and Nifursol.

Figure 7A:
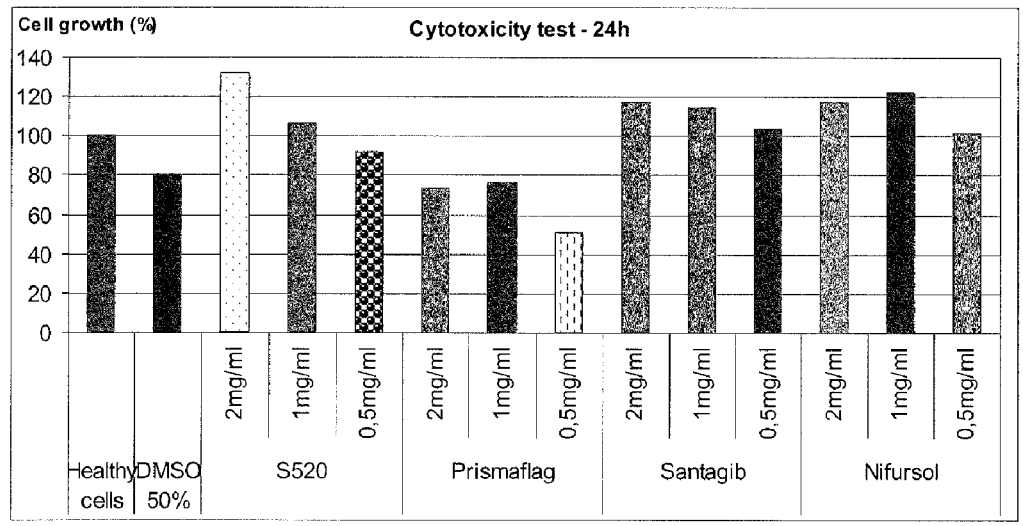
FIG. 7 is a graphical representation comparing the cytotoxicity of the extract according to the invention with reference molecules at 24 h (FIG. 7a) and at 48 h (FIG. 7b).
Figure 7B:
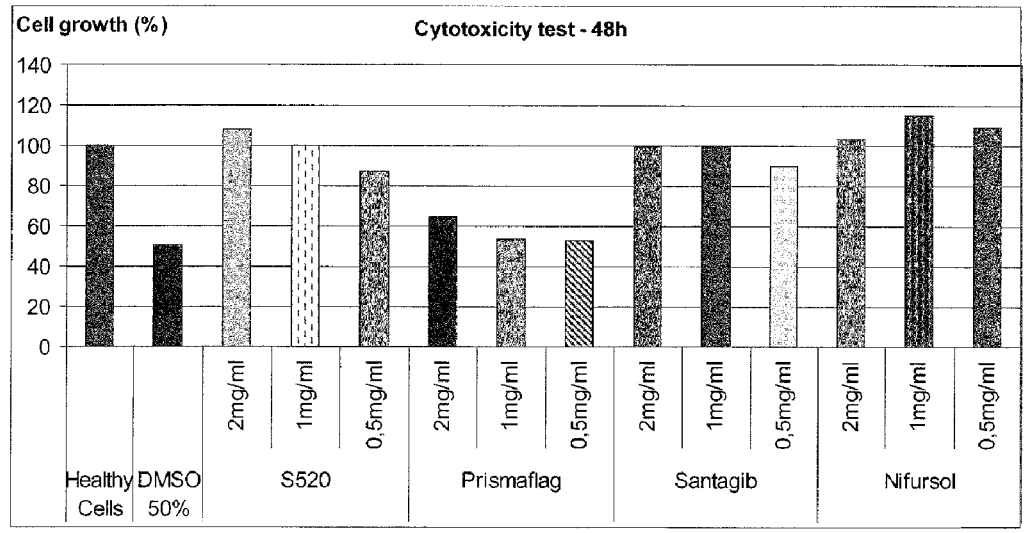

We tested 4 concentrations of each of the extracts: 2 mg/mL, 1 mg/mL, 500 μg/mL and 100 μg/mL (FIGS. 7a and 7b).

Only PrismaFlag® was considered to be cytotoxic since at 500 μg/mL, from 24 h incubation with the cells, it led to less than 60% of cell growth when compared with the control. S520 is not toxic for human cells in culture. The same is true for Santagib® and Nifursol.

2.3. Reverse Mutation Test

For S520 to be used in meat-producing poultry rearing it is essential to ensure that it is not mutagenic (and therefore carcinogenic). S520 was thus tested at 2 mg/mL, 1 mg/mL and 500 μg/mL.

The results are given in the following table:

|  |  | Back-ground | S520 | | |
|---|---|---|---|---|---|
|  |  |  | 2 mg/mL | 1 mg/mL | 500 μg/mL |
| % reverse mutations | Without activation | 54.2 | 14.6 | 7.3 | 10.4 |
|  | With activation | 84.4 | 67.7 | 67.7 | 60.4 |

Without S9 activation, the rate of spontaneous reversion was 54.2%. For the three concentrations of S520 tested, a lower spontaneous reversion rate was obtained.

With S9 activation, the rate of spontaneous reversion was 84.4%. Again this time S520 gave a lower rate.

S520, whether activated or not, is therefore not mutagenic.

2.4 Anti-*Trichomonas vaginalis* Activity of S520

A mix of Hollander medium with added parasites was prepared for each test:

24 volumes of supplemented Hollander medium at 35° C.+1 volume of *T. vaginalis* culture.

S520 was tested at 4 concentrations: 1 mg/mL, 500 μg/mL, 100 μg/mL and 50 μg/mL.

Counts of the *T. vaginalis* cultures were made after 24 h, 48 h and 72 h.

The experiment was performed in triplicate.

Figure 8A:
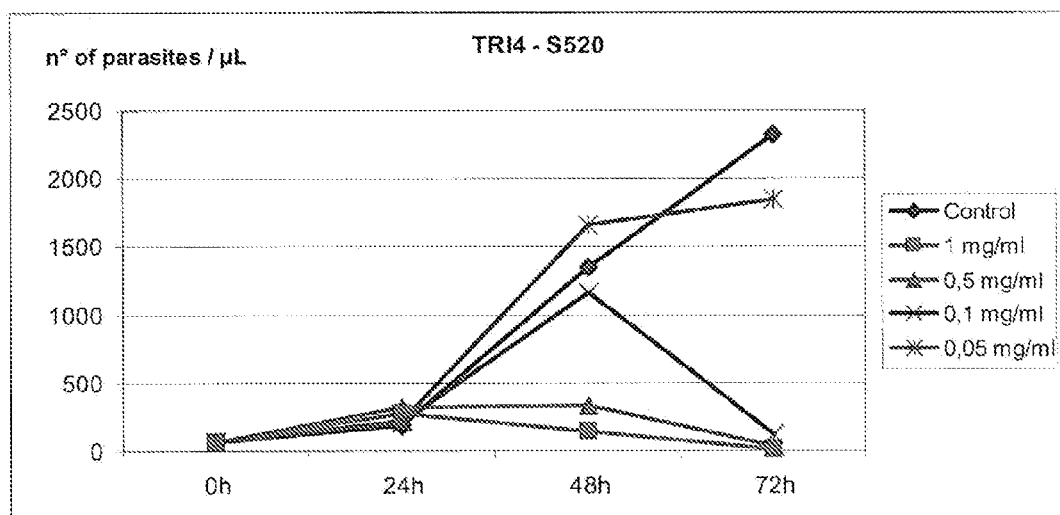
FIG. 8 is a graphical representation of the efficacy of the extract according to the invention on *Trichomonas vaginalis* after 24 h (FIGS. 8a) and 72 h (FIG. 8b).
Figure 8B:
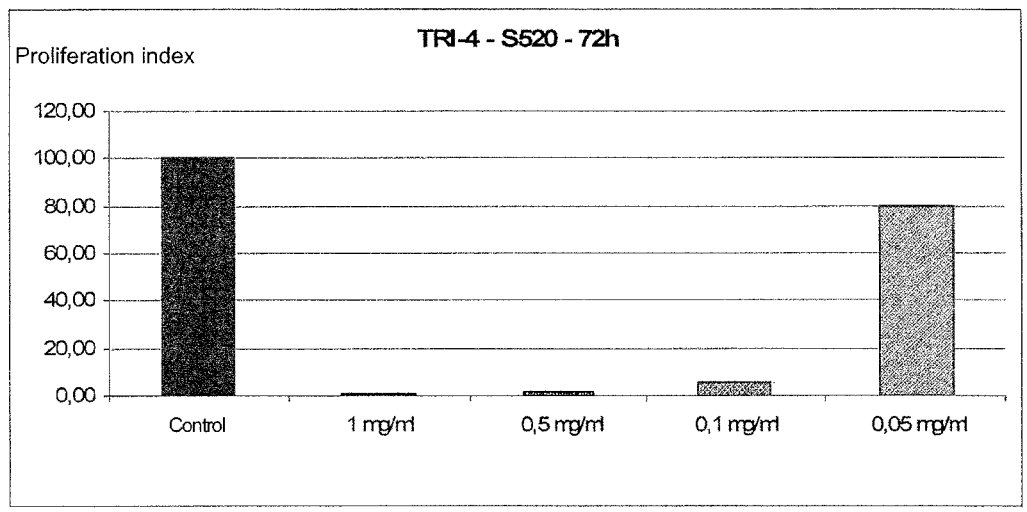

The results (FIGS. 8 and 9) show that S520 is trichomonicidal from 500 μg/mL (1% of growth relative to the control at 72 h).

It is trichomonistatic from 100 μg/mL (5% of growth relative to the control at 72 h).

The invention and the advantages that ensue from it are illustrated well by the previous description. In particular the efficacy should be noted of fenugreek extract on flagellate parasites, particularly when it is in the form of micronised dehusked seeds.

The extract can thus be used for the treatment of diseases such as, in particular, histomoniasis in galliform birds particularly the turkey. It can also be used for the treatment of trichommoniasis in humans. In all cases, it is not only effective but also non-mutagenic and non-cytotoxic.

The invention claimed is:

1. A method for the treatment of human or animal diseases involving flagellated protozoa belonging to the Metamonada phylum, said method comprising the steps of:
    using water to extract an aqueous extract from fenugreek seeds;
    formulating a composition comprising the aqueous extract of fenugreek; and
    administering the composition to a human or animal in need thereof.

2. The method according to claim 1, wherein the diseases involve *Histomonas meleagridis* and *Trichomonas vaginalis*.

3. The method according to claim 1, wherein the diseases involve histomoniasis of galliform birds.

4. The method according to claim 1, wherein the diseases involve *trichomoniasis* in men and/or women.

5. The method according to claim 1, wherein the aqueous extract is obtained from dehusked, micronised or atomised seeds.

6. The method according to claim 1, wherein the aqueous extract is obtained from germs previously separated from seeds after germination.

7. The method according to claim 1, wherein the aqueous extract is incorporated into a dietary supplement or a drink and makes up between 0.1 and 5% by weight of the composition.

8. The method according to the claim 1, wherein the flagellated protozoa is chosen from the group consisting of *Tetratrichomonas gallinarum, Trichomonas gallinae, Trichomonas foetus, Trichomonas equi, Spironucleus vortens, Hexamita meleagridis*, and *Giardia intestinalis*.

9. The method according to claim 3, wherein the galliform birds are turkeys.

* * * * *